United States Patent [19]

Amano et al.

[11] Patent Number: 5,073,485

[45] Date of Patent: Dec. 17, 1991

[54] IMMUNOASSAY METHOD CONDUCTED AT LOW PH

[75] Inventors: Yoshiyuki Amano, Kyoto; Jun-ichiro Kikutake, Ibaraki; Masakazu Sugiura, Kyoto, all of Japan

[73] Assignee: Sanyo Chemical Industries, Ltd., Kyoto, Japan

[21] Appl. No.: 432,916

[22] Filed: Nov. 7, 1989

[30] Foreign Application Priority Data

Nov. 7, 1988 [JP] Japan .................................. 63-280667

[51] Int. Cl.$^5$ .......................................... G01N 33/552
[52] U.S. Cl. ................................... 435/7.94; 436/527; 436/824; 436/825
[58] Field of Search ....................... 436/824, 825, 527; 435/7.94

[56] References Cited

U.S. PATENT DOCUMENTS

4,687,734  8/1987  Chester ................................. 436/824
4,703,001  10/1987  Vodian et al. ...................... 436/825

OTHER PUBLICATIONS

Clin. Chem. 29/2,355(1983) Enzyme Immunoassay for Urinary Albumin, B. A. Fielding, D. A. Price, and C. A. Houlton.
Journal of Immunological Methods, 36(1980) 149–158, A Sandwich Method of Enzyme Immunoassay, III. Assay for Human Beta-2 Microglobulin Compared with Radioimmunoassay, B. Ferrua, C. Vincent, et al.
Clin. Chem. 28/10,2033(1982) $\beta_2$-Microglobulin Determined by Radioimmunoassay with Monoclonal Antibody, R. Swanson, R. Tracy, J. Katzmann, et al.
Bull World Health Organ. 53,55(1976)Enzyme Immunoassays in Diganostic Medicine (Theory and Practice) A. Voller, D. E. Bidwell, and A. Bartlett.
Clin. Chem. 29/7,1437(1983) Enzyme Immunoassay of Thyroxin-Binding Globulin in Dried Blood Samples on Filter Paper, N. Hata, M. Ito, H. Mizuta, et al.

*Primary Examiner*—Christine Nucker
*Assistant Examiner*—Jeffrey Stucker
*Attorney, Agent, or Firm*—Oblon, Spivak, McClelland, Maier & Neustadt

[57] ABSTRACT

An immunoassay method which measures test samples at high concentration without dilution is disclosed. Said immunoassay comprises the steps of: (1) reacting a material (A) to be measured, an immobilized component (B) which binds specifically to the material (A), and a labelled component selected from the group consisting of (i) a labelled component (C) which binds specifically to the material (A) and (ii) a labelled component (A) thereby obtaining an immuno-complex and (2) detecting or measuring the labelling fragment, wherein the reaction of the material (A) with the immobilized (B) or the reaction of the material (A) with the immobilized (B) and the labelled component is carried out at a pH of 2–4.5.

20 Claims, 1 Drawing Sheet

IMMUNOASSAY METHOD CONDUCTED AT LOW PH

BACKGROUND OF THE INVENTION

1. Field of the Invention

This invention relates to an immunoassay method and a test kit.

2. Description of the Prior Art

Known immunoassay methods comprise reacting an immobilized component (B) to bind specifically to a material (A) to be measured. A label can be present in component (B) or component (A). The binding reaction is conducted at a pH of 7-8, followed by measurement of the amount of the label (such as JPN Patent No. 118159/1982).

Among the materials of interest however, are some whose concentration is too high to be measured by these known methods. Since there is a limitation of measurable concentration range in these methods, they have drawbacks in that it is necessary to dilute the test material resulting in a complicated procedure.

SUMMARY OF THE INVENTION

It is an object of the present invention to provide an immunoassay capable of measuring materials even at high concentration.

It is another object of this invention to provide a test kit for immunoassay applicable to materials even at high concentration without dilution.

These and other objects of the present invention have been attained broadly by an immunoassay which comprises the steps of:

(1) reacting a material (A) to be measured, with an immobilized component (B) which binds specifically to the material (A), and with a labelled component selected from the group consisting of (i) a labelled component (C) which binds specifically to the material (A) and (ii) a labelled component (A), to obtain an immunocomplex; and (2) detecting or measuring or determining the labelling fragment, wherein the reaction of the material (A) with the immobilized material (B) or the reaction of the material (A) with the immobilized material (B) and said labelled component, is carried out at a pH of 2-4.5.

DETAILED DESCRIPTION OF THE PREFERRED EMBODIMENTS

Figure 1:
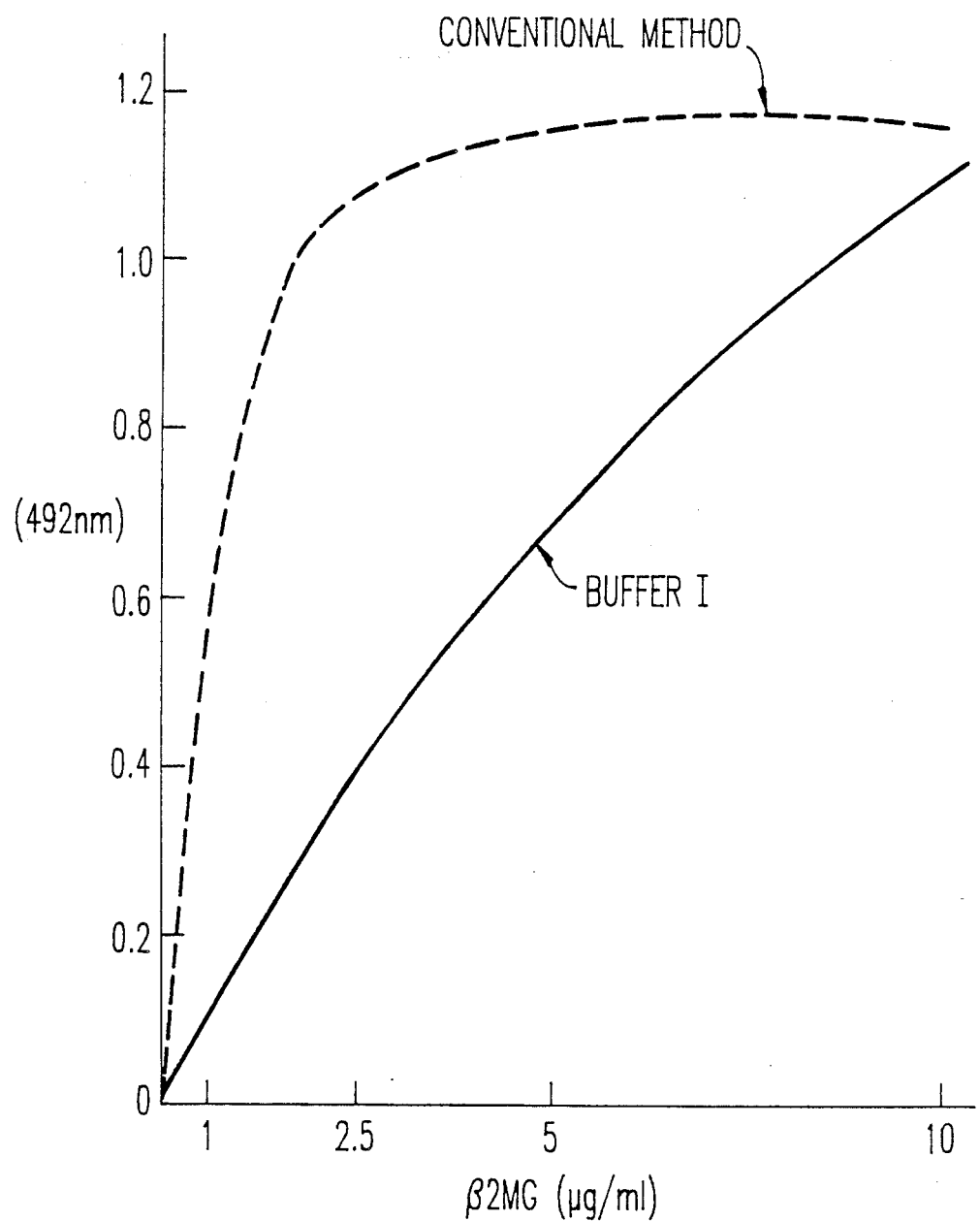
FIG. 1 is beta$_2$ MG standard curve obtained in Example 1, compared with that obtained by a known method.

Suitable materials (A) to be measured include, for example, antigenic substances, enzymes and the like. Illustrative examples of suitable materials employed in the present invention, are 1) serum proteins, such as alpha-foetoprotein (AFP), CEA, IgE, beta$_2$-microglobulin, TBG, IAP, $C_3$, $C_4$, $C_5$, CRP, alpha-microglobulin, alpha$_1$-microglobulin, IgA, IgM, IgG, IgD, HPL, transferrine, sugar proteins, albumin and the like;

2) hormones, such as insulin, human chorionic gonadotropin beta-subunit (HCG-beta), growth hormone, thyroid stimulating hormone (TSH), $T_3$, $T_4$, LH, FSH, prolactine, somatostatine, thyroxine, triiodothyronine and the like;

3) tumor associated antigens, such as carcinoembryonic antigen (CEA), ferritin, POA, CA-19-9, CA125 and the like; and 4) pathogens (pathogenic bacteria, viruses, parasites or protozoas, causing various disease), such as mycobacteria, streptococcus, hepatitis viruses (such as hepatitis B virus), rubella virus, herpes virus, toxoplasma gondii, malarial parasite, amoebic dysentery and the like.

5) enzymes, such as elastase, amylase, proteinase, lipase and the like.

Among these, preferred are serum proteins, particularly those which require dilution, such as AFP, beta$_2$-microglobulin, TBG, IAP, $C_3$, $C_4$, $C_5$, CRP, alpha$_2$-microglobulin, IgA, IgM, IgG, IgD, IgE, HPL and transferrine.

Suitable components (B) include antibodies and antigens which react specifically with the material (A). Examples of (B) are anti-AFP antibody in the case where (A) is AFP antigen, anti-TBG antibody when (A) is TBG antigen, anti-HBs antibody when (A) is HBs antigen, HBs antigen when (A) is anti-HBs antibody, and so on. Among components (B) the preferred are ones have a molecular weight of about 10,000-about 500,000.

Suitable antibodies for this invention include polyclonal antibodies and monoclonal antibodies. Polyclonal antibodies can be obtained by immunizing a mammal (such as rabbit, goat, sheep, guinea pig and the like) with the antigen. Monoclonal antibodies useful in the present invention can be obtained by known process, as described in Nature 256, 495-497, for example. Basically, it involves injecting a mouse or other suitable animal with an immunogen, fusing antibody-producing cells taken from the animal with myeloma cells (originated from a mouse or other suitable animal), and culturing or asciting the resulting hybridoma or hybrid cell. These antibodies may be purified by known methods, such as ammonium-sulfate precipitation, DEAE-cellulose chromatography, affinity chromatography and the like.

Said component (B), can be immobilized on a substrate such as an inorganic or organic carrier (insoluble solid).

Suitable carriers include inorganic carriers, for example, siliceous materials such as glass (porous glass, frosted glass and so on), silica (silica gel, colloidal silica), bentonite, wollastonite, cordierite and the like, and nonsiliceous metal oxides such as alumina, spinel, apatite, hydroxy apatite, titania, zirconia and magnetic substances (such as iron oxides, ferrite, nickel oxides, cobalt oxides and the like); and organic carriers, for instance, plastics such as polystyrene, and derivatives thereof such as poly(amino-styrene); acrylic polymers, such as polyacrylonitrile; polymethacrylates, such as polymethylmethacrylate; polyolefines, such as polyethylene, polypropyrene, polybutene and polybutadiene; halogen-containing polymers, such as poly(vinyl chloride) and poly(vinylidene chloride); polyesters, such as poly(ethylene terephthalate); polyamides, such as nylon 6 and nylon 6,6; and natural polymers, such as polysaccharides, cellulose, dextran, agarose, paper (such as filter paper), polypeptide, collagen and the like. Among these, preferred are glass, plastics, magnetic substances, cellulose and papers.

These carriers may be particulate in nature, varying from a finely divided powder to a coarse granular material (e.g. about 20-about 100 mesh or more, U.S. Standard Sieve), or may be a shaped article, such as sheet or pellet or three-dimensional articles, such as beads, test tubes, trays, discs and so on. Among these, preferred are glass (particularly glass beads and glass test tubes) and plastics (plastic tubes and plastic trays). These carriers may be porous, or surface-modified by known methods, such as etching or frosting, chemical treatment, chemical coating and the like.

The component (B) can be immobilized by any known means, which can vary from simple adsorption to chemical coupling. Chemical coupling typically involves treating the carrier with one or more chemical compounds (silanes, polyisocyanates and the like), followed by contacting the treated carrier with an aqueous solution of (B). Adsorption usually involves contacting an aqueous solution of (B) with the carrier for a time sufficient to permit the desired or maximum degree of immobilization. Examples of methods suitable for the immobilization of component (B) are; physical adsorption or chemical coupling to glass with a silane coupling agent either with or without a crosslinking agent, as described in U.S. Pat. Nos. 4,280,992 and 3,652,761; and those using physical adsorption to plastics, as written in E. Engvall, J. Johnson, P. Parlman: Biochim. Biophys. Acta, 251 (1971) 427–434. Among these methods, preferred are silane coupling and physical adsorption.

Illustrative examples of immobilized components (B) are anti-AFP antibody supported on glass bead, and anti-HBs antibody supported on plastic tray.

The labelled component is selected from (i) a labelled component (C) which binds specifically to the material (A) or (ii) a labelled material (A).

Suitable labelled components (C), hereinafter referred to as label-C, are obtainable by labelling components which bind specifically to the material (A), which components may be the same one as component (B) or different therefrom, and are inclusive of labelled antibodies, labelled antigens, and the like.

Illustrative examples of labelled antigens are labelled serum proteins, such as beta$_2$-microglobulin, TBG, IAP, $C_3$, $C_4$, $C_5$, CRP, alpha$_2$-microglobulin, IgA, IgM, IgG, IgE, IgD, HPL, transferrine, albumin, and the like. Among these, preferred are labelled ones from beta$_2$-microglobulin, TBG, IgE and albumin. Suitable labelled antibodies include, for example, ones from antibodies produced by immunizing mammals with the antigens as mentioned above.

Markers used for labelling include ones usually employed for this purpose. Illustrative examples of suitable markers include isotopes (radioisotopes, such as $I^{125}$ and the like), enzymes (such as peroxidase, beta-galactosidase, alkaline phosphates, and the like), fluorescent substances (such as europeum as europeum derivatives), illuminant substances (such as N-methyl acridium), and so on. Among these, preferred are isotopes and enzymes, more preferred are the latters, particularly peroxidase.

Labelling may be performed by any known methods, for example, enzyme labelling by periodoic acid oxidation methods, as described in Nakane et al, J. Histochem. Cytochem. 22, 1084 (1974); and those described in S. Yoshitake, M. Imagawa, E. Ishikawa, et al, J. Biochem. 92, 1413–1424 (1982).

Suitable labelled materials (A), hereinafter referred to as label-A, include those obtainable from materials (A) as mentioned above, by labelling in the same manner as above. Among label-A, preferred are beta$_2$-microglobulin, TBG and albumin.

Immuno-complexes can be produced by reacting a material (A) with an immobilized material (B), and then, after B/F separation, bonding thereto a label-C or a label-A; by reacting simultaneously a material (A), an immobilized (B) and a label-C; or by reacting simultaneously a material (A), an immobilized (B) and a label-A.

Immnoassay methods for measuring the labelling fragment include any of the known methods, such as RIA using isotopes, EIA using enzymes, FIA using fluorescent substances and ones using illuminant substances.

It is effective in this invention to carry out the reaction of the material (A) with the immobilized material (B) or the reaction of the material (A) with the immobilized material (B) and the labelled component at a pH of usually 2–4.5, preferably 3.5–4.3.

In order to adjust the pH within the range of 2–4.5, one or more buffers are used in the invention, which may be either solid or liquid (buffer solutions) and are not particularly restricted. Any buffer having buffer action between 2–4.5, preferably 3.5–4.3 is suitable Examples of suitable buffer solutions include those comprising combinations of one or more acidic components (such as acetic, hydrochloric, citric, succinic, maleic, barbituric, benzoic and p-hydroxy-benzoic acids and the like) with one or more basic components (such as sodium acetate, $Na_2HPO_4$, $K_2HPO_4$, sodium citrate, KCl, glycine and the like). Among these, the preferred ones are combinations of citric acid with $Na_2HPO_4$ and combinations of sodium acetate with hydrochloric acid, in view of precise measurement. Mole concentration of buffer solutions is preferably at least 0.05M for stabilizing pH, more preferably 0.05–0.3M in view of stability of the measuring systems. Buffers may be added to the reaction systems or reaction mixtures, generally in an amount of at least 0.05M, preferably 0.05–0.3M.

The reaction or incubation to obtain an immuno-complex can be carried out under the usual conditions, except for the pH. For example, at 5°–50° C., preferably 34°–40° C., for 5 minutes–1 day, preferably for 5–60 minutes.

In an embodiment of determining (A), a material (A) and an immobilized component (B) are reacted in a buffer solution of pH 2–4.5 for 5 minutes–1 day. After a certain period of time, B/F separation is carried out to form an complex of the (A) and the immobilized component (B). Then, the resulting complex is reacted with a label-C or a label-A for 5 minutes–1 day to label the complex, followed by carrying out B/F separation and determining the amount of label.

In another embodiment determining (A), a material (A), an immobilized component (B) and a label-C are reacted simultaneously in a buffer solution of pH 2–4.5 for 5 minutes–1 day. After reaction of a certain period of time, B/F separation is carried out to form an immuno-complex of the (A), the immobilized (B) and the label-C. Then, B/F separation is carried out, followed by determining the amount of the label.

In still another embodiment which measures (A), a material (A), an immobilized component (B) and a label-A are reacted simultaneously in a buffer solution of pH 2–4.5 for 5 minutes–1 hour. After reaction for certain period of time, B/F separation is carried out to form complex of the (A), the immobilized (B) and the label-A. Then, B/F separation is carried out, followed by determining the labelling.

In these procedures, B/F separation can be carried out in the usual way, for example, by removing the liquid under suction using an aspirator. Separated solid materials may be washed, for instance with 1–5 ml of a washing liquid (such as distilled water, physiologic saline, a phosphate buffer or the like), and the procedure may be repeated several times (for example, twice–five times) to obtain an immono-complex separated from unreacted materials.

Immunoassay according to the present invention can be applied to detection or determination of materials of even high concentration.

As another aspect, this invention provides test kits for immunoassay applicable to materials even at high concentration without dilution. Such kits of the invention include those comprising 1) an immobilized component (B) binding specifically to said material (A),
2) a labelled component (C) binding specifically to said material (A), and
3) a buffer maintaining the pH at 2–4.5; and those comprising
1) an immobilized component (B) binding specifically to said material (A),
2) a labelled material (A), and
3) a buffer maintaining the pH at 2–4.5.

The inventors have found that by carrying out immuno-reaction at pH of 2–4.5 simple and convenient immunoassay methods can be performed without dilution even where such dilution is required in prior art methods. In addition, the range of calibration can be easily controlled by changing the pH of the reaction mixture, whereby measuring systems of good calibration range can be obtained. Since dilution is not necessary, the invention can provide convenient immunometrical assay methods of wider calibration range, for example, 0.1–20 micro-grams/ml in the case of beta$_2$MG, 1–50 micro-grams/ml in the case of TBG, 1–2000 IU/ml in the case of IgE and 1–60 micro-grams/ml in the case of albumin. Test kits of this invention are useful as diagnostic reagents, having no need of dilution, for beta$_2$MG, TBG, IgE, albumin and the like, which needed dilution heretofore.

Having generally described the invention, a more complete understanding can be obtained by reference to certain specific examples, which are included for purposes of illustration only and are not intended to be limiting unless otherwise specified.

EXAMPLE 1

Determination of Human beta$_2$-Microglobulin a) Preparation of Human beta$_2$-Microglobulin standards solution Concentration of high concentration beta$_2$-Microglobulin solution, obtained from human urea, was detected by beta$_2$-Microglobulin measuring kit [Beta$_2$-Microglobulin, RIA:Pharmacia] followed by diluting the solution with 0.02M tris/HCl buffer containing 0.1% bovine serum albumin(BSA) to obtain standard solution of 1,2.5,5 and 10 μg/ml, respectively.

b) Preparation of anti-beta$_2$-Microglobulin monoclonal antibody

A mouse (Balb/c) was immunized by injecting with a high concentration human beta$_2$-Microglobulin solution. After 6 weeks, a cell suspension was produced from the spleen; and then about $1 \times 10^8$ cells of the spleen and about $2 \times 10^7$ mouse myeloma cells were fused with PEG treatment. The resulting fused cells were cultured in HAT medium, followed by screening to select antibody-producing cells (hybridoma). Afterwards, this hybridoma was grown as monoclone by cloning, followed by asciting the monoclone with a mouse. The result ascites fluid was purified to obtain an antibeta$_2$-Microglobulin monoclonal immunoglobulin.

c) Preparation of Peroxidase-labelled rabit anti beta$_2$-Microglobulin polyclonal antibody An anti-beta$_2$-Microglobulin antibody(Produced by DAKO) was combined with peroxidase according to the periodate method described in J. Histochem.Cytochem.,22;:1084, (1974). Concentration of peroxidase included in this labelled compound was $1.2 \times 10^{-5}$ mol/L.

d) Preparation of Glass beads coated with anti-beta$_2$-Microglobulin monoclonal antibody Anti-beta$_2$-Microglobulin monoclonal antibody was coated onto the surface of glass beads, according to the method of U.S. Pat. No. 3,652,761.

e) Preparation of Buffer (I)

Buffer (I) composition was as follows; 0.1M sodium acetate, 0.1M HCl containing 1% BSA and 0.85% NaCl; this buffer was adjusted to pH of 3.5±0.1.

f) Preparation of Buffer(A)

Buffer (A) composition was as follows; 0.02M sodium phosphate containing 0.5% BSA and 0.85% NaCl; this buffer was adjusted to pH 7.3±0.1. Buffer (A) was employed in all experiments.

g) Preparation of substrate solution

Substrate solution composition was as follows: 0.017M citric acid, 0.033M sodium phosphate, 0.028M o-phenylenediamine, and 0.0053M hydrogen peroxide; this buffer was adjusted to pH 4.9±0.1.

h) Preparation of color development stopping solution

Color development stopping solution composition was 1.5N sulfuric acid solution.

i) Preparation of glass beads washing solution

Glass beads washing solution was 0.85% NaCl aqueous solution.

Measurement of Human beta$_2$-Microglobulin (1) Assay-1

After addition of 20 μl of each human beta$_2$-Microglobulin standard or samples into a separate 13×100 mm test tube, 500 μl of buffer-I were added. Then one glass bead coated with anti-beta$_2$-Microglobulin monoclonal antibody was added to each test tube, followed by incubating each test tube for 60 mins. at 37° C. (first incubation). Then the glass bead was washed 4 times by each time adding 3 ml of washing solution. To the washed bead then was added 300 μl of peroxidase labelled rabbit anti-beta$_2$-Microglobulin polyclonal antibody diluted to 5000 times with buffer-A, followed by incubating for 60 mins. at 37° C. (second incubation). The bead was washed 4 times by each time adding 3 ml of washing solution. To the washed bead then was added, on a timed schedule, 0.5 ml of enzyme substrate solution. After a precise 15-mins incubation period at 37° C., color development was terminated by the addition of 2 ml of stopping solution. The absorbance at 492 nm of each solution was determined spectrophotometrically. The caribration curve (as shown in FIG. 1) was obtained by plotting absorbance vs. beta$_2$-Microglobulin concentration in μg/ml. Beta$_2$-Microglobulin concentration of each sample was determined by using this calibration curve.

EXAMPLE 2

Determination of Human TBG a) Preparation of Human TBG standards solution

Concentration of high concentration TBG solution, obtained from human serum, was detected by TBG in measeurng kit (TBG, RIA:EIKEN) followed by diluting the solution with 0.02M sodium phosphate buffer containing 1.0% BSA to obtain standard solutions of 5, 10, 25 and 40 μg/ml, respectively.

b) Preparation of Peroxidase-labelled rabit anti TBG polyclonal antibody

An anti-TBG antibody (Produced by DAKO) was combined with peroxidase according to the periodate method described in J. Histochem.Cytochem..22;:1084, (1974). Concentration of peroxidase included in this labelled compound was $0.8 \times 10^{-5}$ mol/L.

c) Preparation of Glass beads coated with goat anti-TBG polyclonal antibody Anti-TBG antibody (Produced by ATAB) was coated onto the surface of glass beads, according to the method of U.S. Pat. No. 3,652,761.

d) Preparation of Buffer (II)

Buffer (II) composition was as follows; 0.15M Na$_2$HPO$_4$, 0.12M citrate containing 1%BSA and 0.85%NaCl; this buffer was adjusted to pH $4.0\pm0.1$.

e) Preparation of Buffer (A)

Example 1-f) was repeated.

f) Preparation of substrate solution

Example 1-g) was repeated.

g) Preparation of color development stopping solution

Example 1-h) was repeated.

h) Preparation of glass beads washing solution

Example 1-i) was repeated.

Masurement of Human TBG

(1) Assay-2

After addition of one glass bead coated with anti-TBG antibody in a separate 13×100 mm test tube, 500 μl of buffer-II were added. Then human TBG standards or samples were added to each test tube. Followed by incubating each test tube for 30 mins. at 37° C. (first incubation). Then the glass bead was washed 4 times by each time adding 3 ml of washing solution. To the washed bead then was added 300 μl of peroxidase labelled rabbit anti-TBG polyclonal antiboy diluted to 4000 times with buffer-A, followed by incubating for 30 mins. at 37° C. (second incubation). The bead was washed 4 times by each time adding 3 ml of washing solution. To the washed bead then was added, on a timed schedule, 0.5 ml of enzyme substrate solution. After a precise 15-mins incubation period at 37° C., color development was terminated by the addition of 2 ml of stopping solution. The absorbance at 492 nm of each solution was determined spectrophotometrically. The caribration curve was obtained by plotting absorbance vs. TBG concentration in μg/ml. TBG concentration of each sample was determined by using this calibration curve.

EXAMPLE 3

Determination of Human IgE a) Preparation of Human IgE standards solution

Concentration of high concentration IgE solution, obtained from human serum, was detected by using IgE International Reference Standard (No. 68/341) of WHO, with use of a IgE-measuring kit (IgE-RIA, DAINABOTO) followed by diluting the solution with 0.02M sodium phosphate buffer containing 50% horse serum to obtain standard solutions of 50, 200, 500, 1000 and 2000 IU/ml, respectively.

b) Preparation of Peroxidase-labelled rabit anti IgE polyclonal antibody

An anti-IgE antibody (Produced by DAKO) was combined with peroxidase according to the periodate method described in J.Histochem.Cytochem..22;:1084, (1974). Concentration of peroxidase included in this labelled compound was $1 \times 1^{-5}$ mol/L c) Preparation of anti-IgE monoclonal antibody

A mouse (Balb/c) was immuninized by injecting with a high concentration human IgE solution. After 6 weeks, a cell suspension was produced from the spleen; and then about $1 \times 10^8$ cells of the spleen and about $2 \times 10^7$ mouse myeloma cells were fused with PEG treatment. The rusulting fused cells were cultured in HAT medium, followed by screening to select antibody-producing cells (hybridoma). Afterwards, this hybridoma was grown as monoclone by cloning, followed by asciting the monoclone with a mouse. The result ascites fluid was purified to obtain an anti-IgE monoclonal immunoglobulin.

d) Preparation of Glass beads coated with anti-IgE monoclonal antibody

Anti-IgE antibody was coated onto the surface of glass beads, according to the method of U.S. Pat. No. 3,652,761.

e) Preparation of Buffer (III)

Buffer (III) composition was as follows; 0.18M Glycine, 0.02M HCl containing 1%BSA and 0.85%NaCl; this buffer was adjusted to pH $3.5\pm0.1$.

f) Preparation of Buffer(A)

Example 1-f) was repeated.

g) Preparation of substrate solution

Example 1-g) was repeated.

h) Preparation of color development stopping solution

Example 1-h) was repeated.

i) Preparation of glass beads washing solution

Example 1-i) was repeated.

Masurement of Human IgE (1) Assay-3

After addition of one glass bead coated with anti-IgE monoclonal antibody in a separate 13×100 mm test tube, 450 μl of buffer-III were added. Then human IgE standards or samples were added to each test tube, followed by incubating each test tube for 15 mins. at 37° C. (first incubation). Then the glass bead was washed 4 times by each time adding 3 ml of washing solution. To the washed bead then was added 300 μl of peroxidase labelled rabbit anti-IgE polyclonal antiboy diluted to 4000 times with buffer-A, followed by incubating for 15 mins. at 37° C. (second incubation). The bead was washed 4 times by each time adding 3 ml of washing solution. To the washed bead then was added, on a timed schedule, 0.5 ml of enzyme substrate solution. After a precise 15-mins incubation period at 37° C., color development was terminated by the addition of 2 ml of stopping solution. The absorbance at 492 nm of each solution was determined spectrophotometrically. The caribration curve was obtained by plotting absorbance vs. IgE concentration in IU/ml. IgE concentration of each sample was determined by using this calibration curve.

EXAMPLE 4

Determination of Human Urinary Albumin a) Preparation of Human Urinary albumin standards solution Concentration of high concentration human albumin solution, obtained from human serum, was detected by albumin measeurng kit (Albumin,RIA:Pharmacia) followed by diluting the solution with 0.02M sodium phospate buffer containing 0.1% BSA to obtain standard solutions of 5, 10, 30 and 60 mg/l, respectively.

b) Preparation of Peroxidase-labelled Goat anti Urinary albumin polyclonal antibody An anti-Urea albumin antibody (Produced by ATAB) was combined with peroxidase according to the periodate method described in J.Histochem.Cytochem.,22;:1084, (1974). Concentration of peroxidase included in this labelled compound was $1.2 \times 10^{-5}$ mol/L c) Preparation of anti-albumin monoclonal antibody A mouse (Balb/c) was immuninized by injecting with a high concentration human albumin solution. After 6 weeks, a cell suspension was produced from the spleen; and then about $1 \times 10^8$ cells of the spleen and about $2 \times 10^7$ mouse myeloma cells were fused with PEG treatment. The rusulting fused cells were cultured in HAT medium, followed by screening to select antibody-producing cells (hybridoma). Afterwards, this hybridoma was grown as monoclone by cloning, following by asciting the monoclone with a mouse. The result ascites fluid was purified to obtain an anti-albumin monoclonal immunoglobulin.

d) Preparation of Glass beads coated with anti-albumin monoclonal antibody

Anti-albumin antibody were coated onto the surface of glass beads, according to the method of U.S. Pat. No. 3,652,761.

e) Preparation of Buffer (IV)

Buffer (IV) composition was as follows; 0.22M citrate, 0.03M sodium acetate containing 0.5%BSA and 0.85%NaCl; this buffer was adjusted to pH 3.8±0.1.

f) Preparation of Buffer(A)

Example 1-f) was repeated.

g) Preparation of substrate solution

Example 1-g) was repeated.

h) Preparation of color development stopping solution

Example 1-h) was repeated.

i) Preparation of glass beads washing solution

Example 1-i) was repeated.

Measurement of Human Urinary Albumin (1) Assay-4

After addition of 20 μl of each human albumin standard or samples in a separate 13×100 mm test tube, 500 μl of buffer-IV were added. Then one glass bead coated with anti-albumin monoclonal antibody was added to each test tube, followed by incubating each test tube for 15 mins. at 37° C. (first incubation). Then the glass bead was washed 4 times by each time adding 3 ml of washing solution. To the washed bead then was added 300 μl of peroxidase labelled goat anti-albumin polyclonal antiboy diluted to 4000 times with buffer-A, followed by incubating for 15 mins. at 37° C. (second incubation). The bead was washed 4 times by each time adding 3 ml of washing solution. To the washed bead then was added, on a timed schedule, 0.5 ml of enzyme substrate solution. After a precise 15-mins incubation period at 37° C., color development was terminated by the addition of 2 ml of stopping solution. The absorbance at 492 nm of each solution was determined spectrophotometrically. The caribration curve was obtained by plotting absorbance vs. albumin concentration in μg/ml. Albumin concentration of each sample was determined by using this calibration curve.

What is claimed as new and desired to be secured by Letters Patent is:

1. An immunoassay method, which comprises the steps of:
   (1) reacting a material (A) to be measured, an immobilized component (B) which binds specifically to the material (A), and a labelled component selected from the group consisting of
      (i) a labelled component (C) which binds specifically to the material (A) and
      (ii) a labelled material (A*) formed by labelling the same material as the material (A), thereby obtaining an immuno-complex; and
   (2) detecting or determining the labelling fragment, wherein the reaction of the material (A) with the immobilized component (B) or the reaction of the material (A) with the immobilized component (B) and said labelled component is carried out at a pH of 2-4.5 and a temperature not more than 50° C., the pH being adjusted with a buffer containing an acid component selected from the group consisting of acetic, hydrochloric, succinic, maleic, barbituric, benzoic and p-hydroxy-benzoic acids, wherein at least one, of (A) and (B) is an antigen or an antibody.

2. The method of claim 1, wherein the material (A) is reacted with the immobilized component (B) at a pH of 2-4.5, thereby obtaining an immune-complex.

3. The method of claim 1, wherein the material (A) is reacted with the immobilized component (B) and the labelled component at a pH of 2-4.5, thereby obtaining an immuno-complex.

4. The method of claim 1, wherein the labelled component is a labelled component (C).

5. The method of claim 1, wherein the labelled component is a labelled material (A).

6. The method of claim 1, which comprises adding the material (A) to a buffer thereby maintaining the pH at 2-4.5, and adding said immobilized component (B).

7. The method of claim 1, which comprises adding said immobilized component (B) to a buffer thereby maintaining the pH at 2-4.5, and adding the material (A).

8. The method of claim 1, which comprises adding the material (A) to a buffer thereby maintaining the pH at 2-4.5, adding the labelled component, and adding said immobilized component (B).

9. The method of claim 8, wherein the labelled component is a labelled component (C).

10. The method of claim 8, wherein the labelled component is a labelled material (A).

11. The method of claim 1, which comprises adding said immobilized component (B) to a buffer thereby maintaining the pH at 2-4.5, adding the labelled component, and adding the material (A).

12. The method of claim 11, wherein the labelled component is a labelled component (C).

13. The method of claim 11, wherein the labelled component is a labelled material (A).

14. The method of claim 1, wherein said material (A) is an antigen or an antibody.

15. The method of claim 1, wherein said material (A) is at least one material selected from the group consisting of serum-proteins, hormones, bacteria and viruses.

16. The method of claim 1, wherein said material (B) is an antibody or an antigen.

17. The method of claim 1, wherein the labelled component has been labelled with a marker selected from the group consisting of isotopes, enzymes, fluorescent substances and illuminant substances.

18. The method of claim 1, wherein the labelled component has been labelled with an enzyme.

19. A kit for the detection or determination of a material (A) to be measured, which comprises
1) an immobilized component (B) which binds specifically to said material (A),
2) a labelled component (C) which binds specifically to said material (A), and
3) a buffer which maintains the pH at 2-4.5 during the binding reaction.

20. A kit for the detection or determination of a material (A) to be measured, which comprises
1) an immobilized component (B) which binds specifically to said material (A),
2) a labelled material (A), and
3) a buffer which maintains the pH at 2-4.5 during the binding reaction.

* * * * *